United States Patent [19]

Pitt et al.

[11] 4,146,799

[45] Mar. 27, 1979

[54] OIL CONCENTRATION DETECTOR

[75] Inventors: Gillies D. Pitt, Harlow; Harry J. Smith, Sawbridgeworth, both of England

[73] Assignee: ITT Industries, Inc., New York, N.Y.

[21] Appl. No.: 844,220

[22] Filed: Oct. 21, 1977

[30] Foreign Application Priority Data

Oct. 29, 1976 [GB] United Kingdom ............... 45204/76

[51] Int. Cl.$^2$ ............................................. G01N 21/26
[52] U.S. Cl. .................................. 250/574; 250/575; 356/343; 356/442
[58] Field of Search ............... 250/573, 574, 575, 209, 250/214 AG; 356/201, 204, 205, 206, 207, 208

[56] References Cited

U.S. PATENT DOCUMENTS

| 3,872,315 | 3/1975 | Boll | 250/575 |
| 3,922,088 | 11/1975 | Lübbers et al. | 250/574 |
| 3,955,096 | 5/1976 | Faulhaber | 356/205 |

*Primary Examiner*—David C. Nelms
*Attorney, Agent, or Firm*—A. Donald Stolzy

[57] ABSTRACT

Apparatus for detecting oil in water contained in a chamber, wherein a semiconductor laser directs infrared radiation into the chamber. The radiation is scattered and detected by one or more cells. The output of one cell controls the gain of an amplifier connected from another cell. In one arragement, the outputs of two cells are connected to a differential amplifier, and the output of the differential amplifier is gain controlled by the output of a third cell.

3 Claims, 4 Drawing Figures

OIL CONCENTRATION DETECTOR

BACKGROUND OF THE INVENTION

This invention relates to an arrangement for measuring the level of oil pollution in water, and more particularly to an infrared light scattering measurement system.

In many situations, such as in the discharge of water ballast from an oil tanker, it is necessary to measure the level of oil pollution in flowing water. The oil, which is generally in the form of finely dispersed droplets, is often measured by directing light from a diffuse visible source through the water and measuring scattered light at an angle to the incident beam. Whilst this method is simple and reasonably effective, it suffers from the disadvantage that deposition of dirt on the detection system reduces the incident light and can cause false readings to be produced. Furthermore, it is difficult with conventional light sources to produce a light beam intense enough for the detector to respond to low oil levels. Such a detector also gives a false reading when suspended solids, e.g. rust particles, are present in the fluid stream.

SUMMARY OF THE INVENTION

According to one aspect of the present invention, there is provided an oil concentration detector, said detector comprising: a scatter cell to hold a mixture of oil and water; a semiconductor laser having an output, said laser producing an electromagnetic wave within the infrared spectrum at said output thereof; a source connected to said laser to activate the same, said scatter cell having at least first, second and third wall portions transparent at least to a portion of said infrared spectrum, said laser being positioned to direct said wave through said first wall portion; first and second cells positioned to receive and responsive to radiation in said spectrum portion to detect such radiation when scattered from oil droplets in water in said scatter cell through said second and third wall portions, respectively, said second and third wall portions being aligned with said first and second cells; an automatic gain control (AGC) amplifier, and utilization means connected in succession in that order; first means connecting said first cell to said AGC amplifier; second means connecting said AGC amplifier to said utilization means; and AGC circuit means connecting said second cell to said AGC amplifier.

According to another aspect of the present invention, there is provided an oil concentration detector, said detector comprising: a scatter cell to hold a mixture of oil and water; a semiconductor laser having an output, said laser producing an electromagnetic wave within the infrared spectrum at said output thereof; a source connected to said laser to activate the same, said scatter cell having at least first, second, third and fourth wall portions transparent at least to a portion of said infrared spectrum, said laser being positioned to direct said wave through said first wall portion; first, second and third cells positioned to receive and responsive to radiation in said spectrum portion to detect such radiation when scattered from oil droplets in water in said scatter cell through said second, third and fourth wall portions, respectively, said third wall portion and said second cell being aligned with and receiving radiation from said laser output entering said scatter cell through said first wall portion; a differential amplifier having inverting and noninverting inputs, and an output; first means connecting said first cell to said noninverting input; an automatic gain control (AGC) amplifier, connection means, and utilization means connected in succession in that order from the output of said differential amplifier; AGC circuit means connecting said second cell to said AGC amplifier; and third means connecting said thrid cell to said inverting input.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
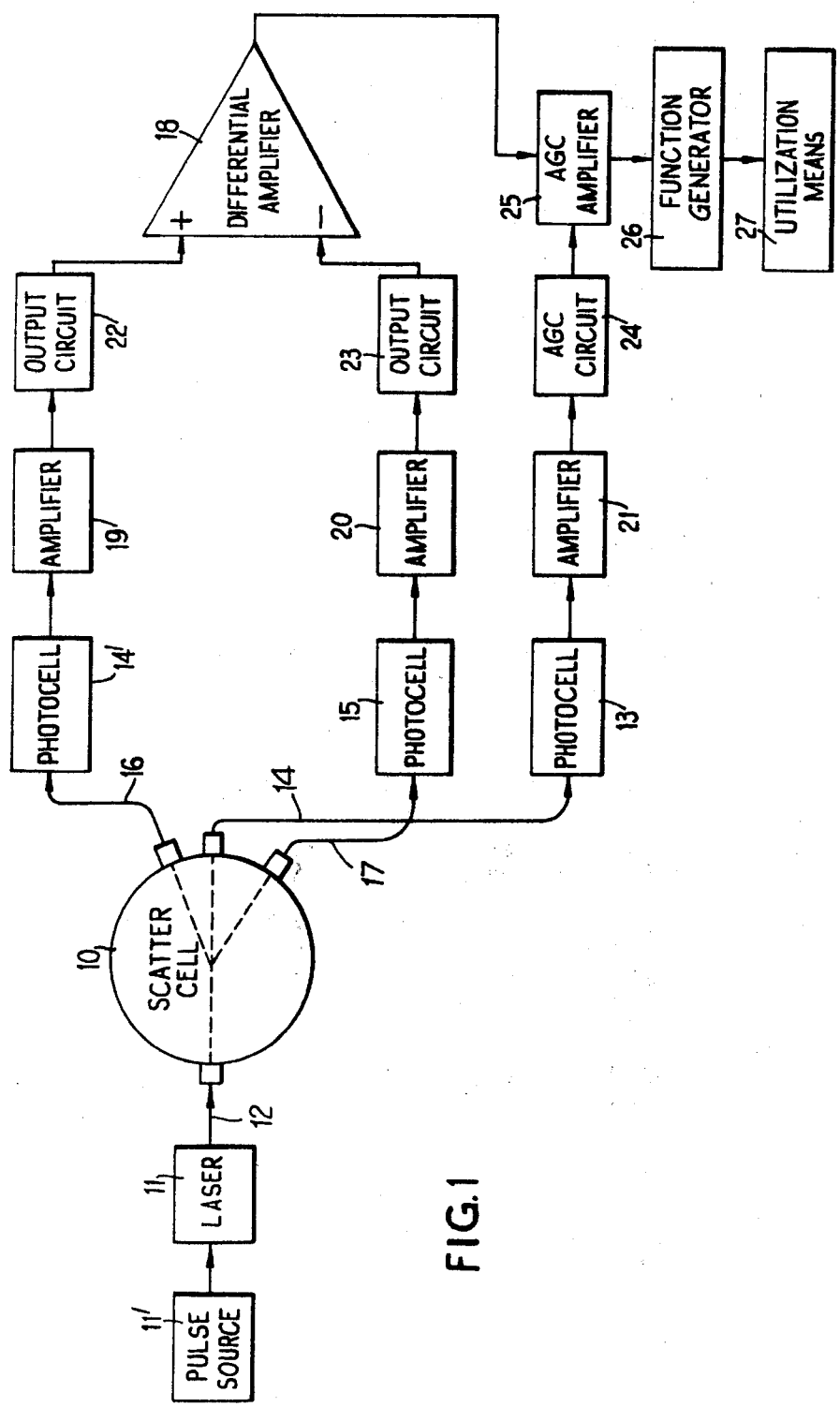
FIG. 1 is a block diagram of an infrared oil detector arrangement employing both absorption and scattering measurement techniques.
Figure 2:
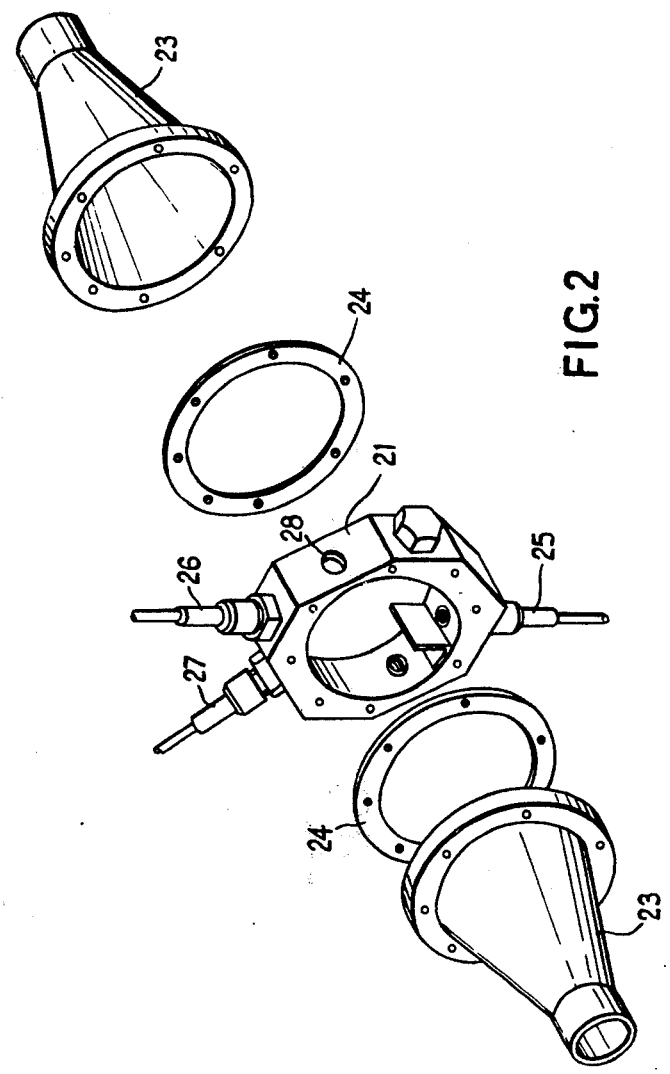
FIG. 2 is an exploded perspective view of a scatter cell shown in the arrangement of FIG. 1.

Referring to FIGS. 1 and 2, the oil detector arrangement of the present invention is fitted to a cell 10 placed in a fluid conduit. A semiconductor infrared laser 11 is operated by a pulse source 11'. The cell 10 may be of the GaAlAs or GaAlP type. It is coupled to a window in the cell 10 via a fiber optic system 12. It transmits light across the cell 10 to a laser output level detector or photocell 13 via a fiber optic system 14 arranged in line with the laser incident beam. One or more light scattering detectors 14, 15 are also provided with respective fiber optic systems 16, 17 arranged at a relatively small angle, e.g. 20°, to the laser incident beam. The outputs of photocells 13, 14' and 15 are fed via amplifiers 19, 20 and 21, respectively, and output circuits 22, 23 and AGC circuit 24, respectively. The outputs or circuits 22 and 23 are connected to the input of differential amplifier 18. An AGC amplifier 25 is connected from amplifier 18 through function generator 26 to utilization means 27. The amplifier 25 is controlled in accordance with the output signal level of photocell 13 via AGC circuit 24. In this way the system of the present invention automatically compensates for changes in the laser output caused by aging or by the presence of obscuring matter on the windows of scatter cell 10. In this way a continuous corrected oil level reading is obtained by means 27 (a voltmeter calibrated in concentration, a process controller or otherwise).

In some applications a second light scattering detector 15, arranged at the same angle to the laser beam as the first detector 14' may be employed to nullify the small perturbation effect caused by the presence of rust particles in the stream. In this arrangement the laser output is polarized and a corresponding crossed polarizing filter is fitted to the second detector 15. As the rust particles rotate the plane of polarization of the incident light, the second detector 15 measures solid particle scattered light only. The outputs of the two scattering detectors 14' and 15 are compared by amplifier 18 (a subtract circuit) to give a corrected oil reading.

A suitable scatter cell construction is shown in FIG. 2. The cell body 21 is mounted between pipe coupling members 23 via gaskets 24 and has a light inlet coupling 25 for the laser and outlet couplings 26 and 27 for two scattering detectors. A window is illustrated at 28.

Source 11' and laser 11 may be entirely conventional.

Figure 3:
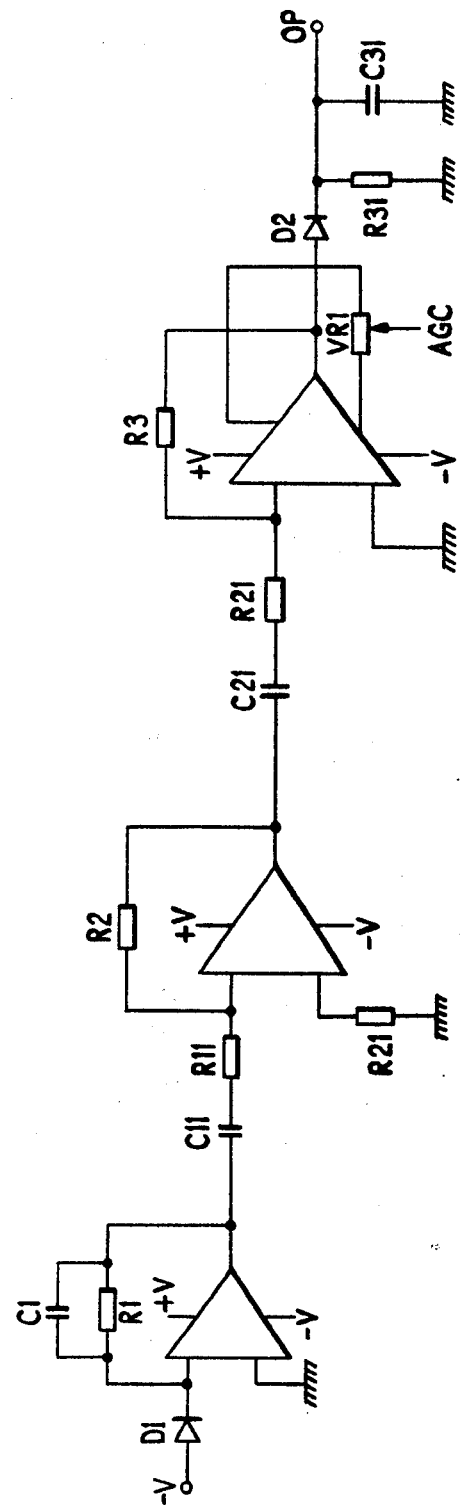
FIG. 3 is a schematic diagram of an output circuit shown in FIG. 1.

Each output circuit 22 and 23 may be as shown in FIG. 3, comprising three A.C. coupled input operational amplifiers. As the reverse bias diode current of the input photodetector D1 has a substantially linear response to incident light falling on its surface, the first stage operates as a current to voltage converter. The signal is further amplified by the second and third operational amplifier stages, which also introduce a time constant of about 1 second, before being applied to a meter or chart recorder.

The output and circuits and source 11' described are given as examples only and other similar circuits may of course be employed.

Figure 4:
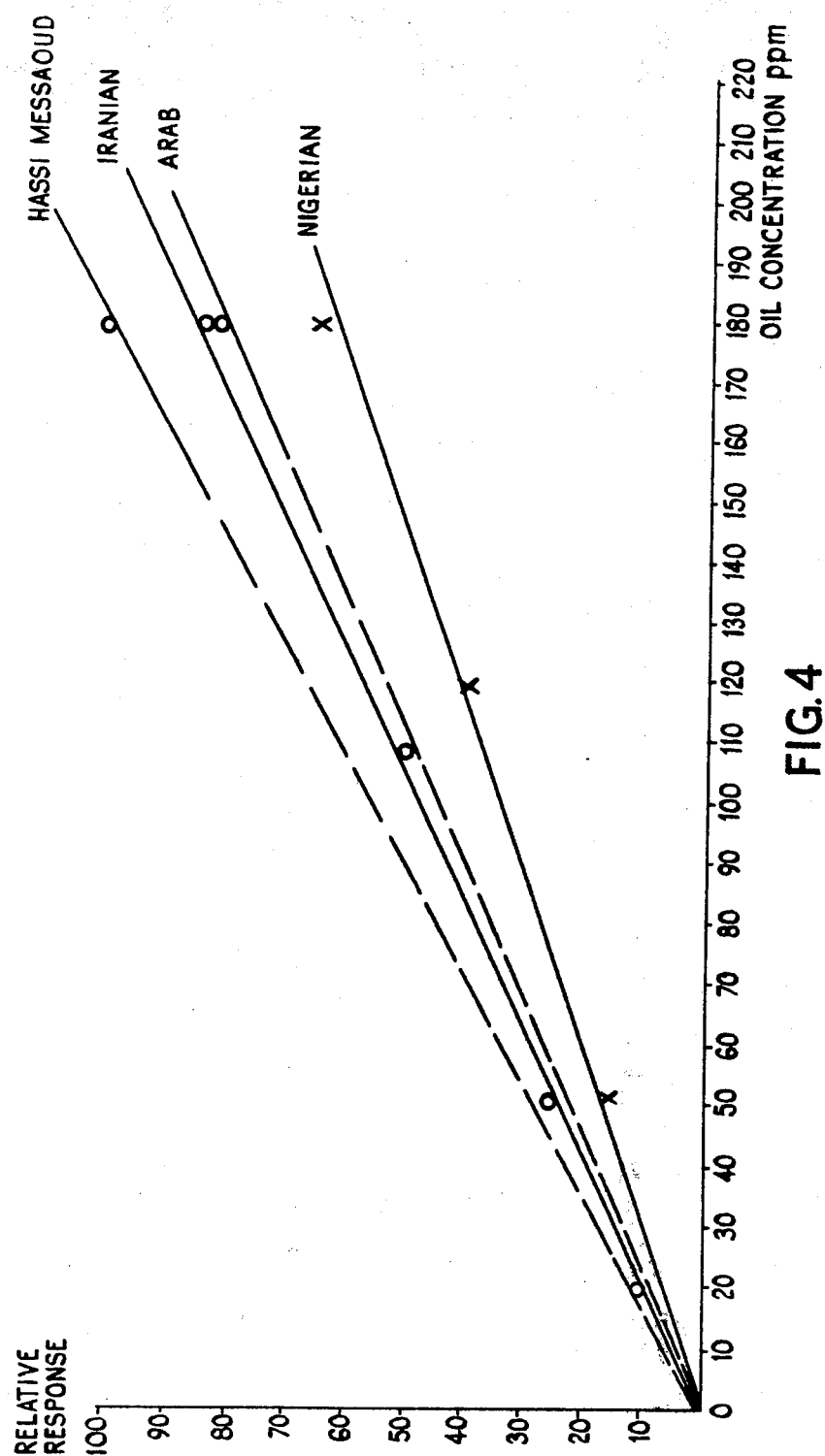
FIG. 4 is a graph showing the response of the detector of FIG. 1 to various types of crude oil.

The response of the system of the present invention varies according to the type of oil present in the water. This effect is shown in FIG. 4 which indicates the relative response of the detector to various types of crude oil.

Owing to the scouring action of the fluid through the cell, it is not necessary to provide any form of window cleaning, particularly as the arrangement automatically compensates for the presence of obscuring matter. However, in some applications the windows may be provided with clean water jets to maintain cleanliness. The windows are, of course, of an infrared transparent material such as quartz or silicon.

In some applications the arrangement of the invention may be protected against overloading by excessive quantities of oil in the water by another photocell for coarse detection arranged upstream and adapted to operate a by-pass valve when excessive oil levels are encountered.

Although the arrangement of the invention has been described with reference to gallium aluminium arsenide and gallium aluminium phosphide lasers, it is not, of course, so limited. Other semiconductor lasers may also be employed provided that the material has a band width greater than 0.5 eV. In other applications a solid state laser operating in the visible region of the spectrum may be employed, although infrared operation is preferable to minimize the effect of suspended solid particles in the fluid stream.

Circuit 24 and amplifier 25 both may be entirely conventional. The same is true of each individual circuit disclosed herein and each individual component thereof, but not the circuit combination.

Solid state lasers e.g. of the gallium aluminium arsenide type can be operated in the infrared region at wavelengths between 8,500 and 9,200 angstroms. They are ideally suited for supplying an intense monochromatic light beam for light scattering measurements. Moreover, by performing the measurements in the infrared spectrum, and at a relatively small angle to the incident beam, the effect of rust particles in the fluid stream is very much reduced, in some cases by an order of magnitude.

What is claimed is:

1. An oil concentration detector, said detector comprising: a scatter cell to hold a mixture of oil and water; a semiconductor laser having an output, said laser producing an electromagnetic wave within the infrared spectrum at said output thereof; a source connected to said laser to activate the same, said scatter cell having at least first, second and third wall portions transparent at least to a portion of said infrared spectrum, said laser being positioned to direct said wave through said first wall portion; first and second cells positioned to receive and responsive to radiation in said spectrum portion to detect such radiation when scattered from oil droplets in water in said scatter cell through said second and third wall portions, respectively, said second and third wall portions being aligned with said first and second cells; an automatic gain control (AGC) amplifier, and utilization means connected in succession in that order; first means connecting said first cell to said AGC amplifier; second means connecting said AGC amplifier to said utilization means; and AGC circuit means connecting said second cell to said AGC amplifier.

2. An oil concentration detector, said detector comprising: a scatter cell to hold a mixture of oil and water; a semiconductor laser having an output, said laser producing an electromagnetic wave within the infrared spectrum at said output thereof; a source connected to said laser to activate the same, said scatter cell having at least first, second, third and fourth wall portions transparent at least to a portion of said infrared spectrum, said laser being positoned to direct said wave through said first wall portion; first, second and third cells positioned to receive and responsive to radiation in said spectrum portion to detect such radiation when scattered from oil droplets in water in said scatter cell through said second, third and fourth wall portions, respectively, said thrid wall portion and said second cell being aligned with and receiving radiation from said laser output entering said scatter cell through said first wall portion; a differential amplifier having inverting and noninverting inputs, and an output; first means connecting said first cell to said noninverting input; an automatic gain control (AGC) amplifier, connection means, and utilization means connected in succession in that order from the output of said differential amplifier; AGC circuit means connecting said second cell to said AGC amplifier; and third means connecting said third cell to said inverting input.

3. The invention as defined in claim 1, wherein said connection means includes a function generator.

* * * * *